United States Patent
Chambers et al.

(10) Patent No.: US 6,174,315 B1
(45) Date of Patent: *Jan. 16, 2001

(54) SPRING BIASED DEFORMABLE INTRAOCULAR INJECTING APPARATUS

(75) Inventors: Thomas J. Chambers, Upland; Vladimir Feingold, Laguna Niguel; Daniel C. Eagles, Capistrano Beach, all of CA (US)

(73) Assignee: STAAR Surgical Company, Inc., Monrovia, CA (US)

(*) Notice: Under 35 U.S.C. 154(b), the term of this patent shall be extended for 0 days.

This patent is subject to a terminal disclaimer.

(21) Appl. No.: 09/195,448

(22) Filed: Nov. 18, 1998

Related U.S. Application Data

(63) Continuation of application No. 08/691,490, filed on Aug. 2, 1996, now Pat. No. 5,860,984, and a continuation-in-part of application No. 08/570,564, filed on Dec. 11, 1995, now Pat. No. 5,772,666, and a continuation-in-part of application No. 08/368,792, filed on Jan. 4, 1995, and a continuation-in-part of application No. 08/196,855, filed on Feb. 15, 1994, now Pat. No. 5,941,886.

(51) Int. Cl.[7] .................................................. A61F 9/00
(52) U.S. Cl. ................................... 606/107; 623/4; 623/6
(58) Field of Search .............................. 623/4, 6; 606/107

(56) References Cited

U.S. PATENT DOCUMENTS

| 834,261 | * | 10/1906 | Chambers | 604/63 |
|---|---|---|---|---|
| 5,304,182 | * | 4/1994 | Rheinish et al. | 606/107 |
| 5,766,181 | | 6/1998 | Chambers et al. | 606/107 |
| 5,772,666 | * | 6/1998 | Feingold et al. | 606/107 |
| 5,860,984 | * | 1/1999 | Chambers et al. | 606/107 |

* cited by examiner

*Primary Examiner*—Glenn K. Dawson
(74) *Attorney, Agent, or Firm*—Law Offices of William L. Klima, P.L.C.

(57) ABSTRACT

A deformable intraocular lens injecting apparatus including a spring biased plunger. A preferred embodiment of the lens injecting apparatus includes a separate lens injecting device having a lens cartridge receiver, and a separate one-piece lens cartridge having a lens holding portion connected to a nozzle portion. The lens cartridge is preferably connected into the lens cartridge receiver by a bayonet-type connection.

17 Claims, 6 Drawing Sheets

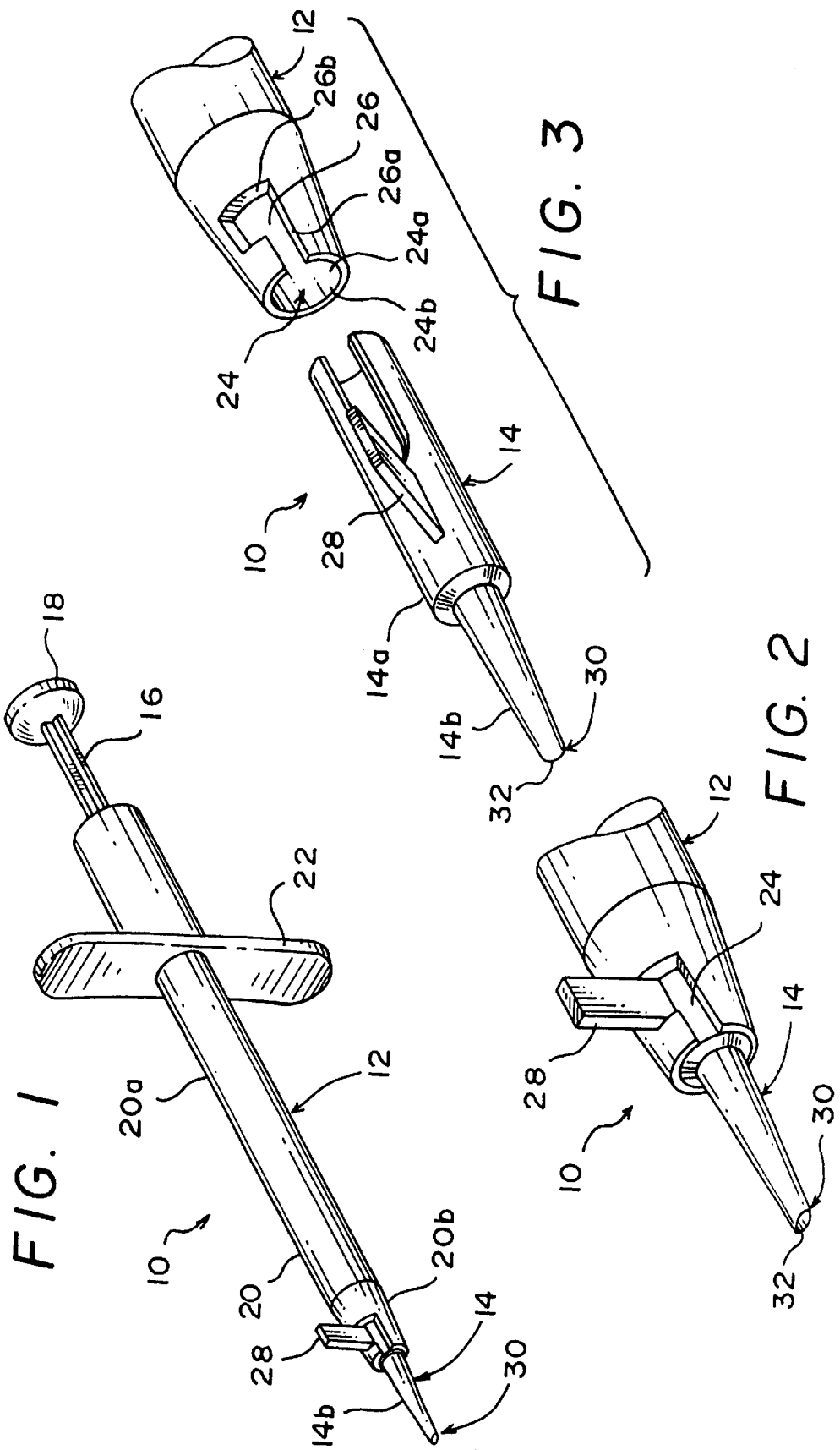

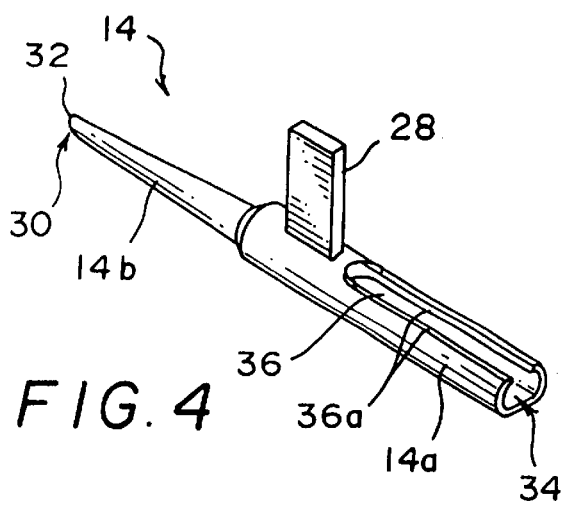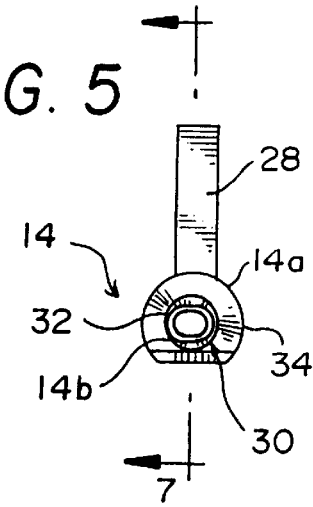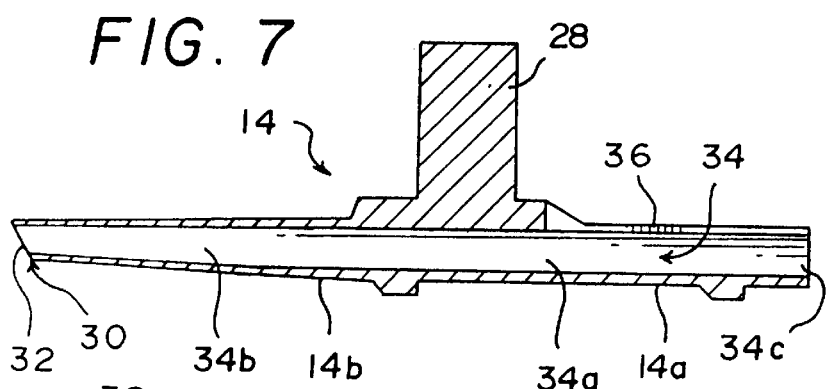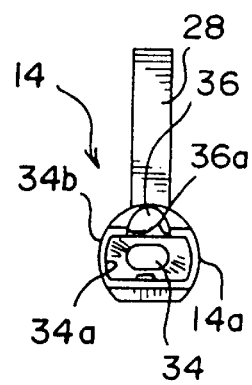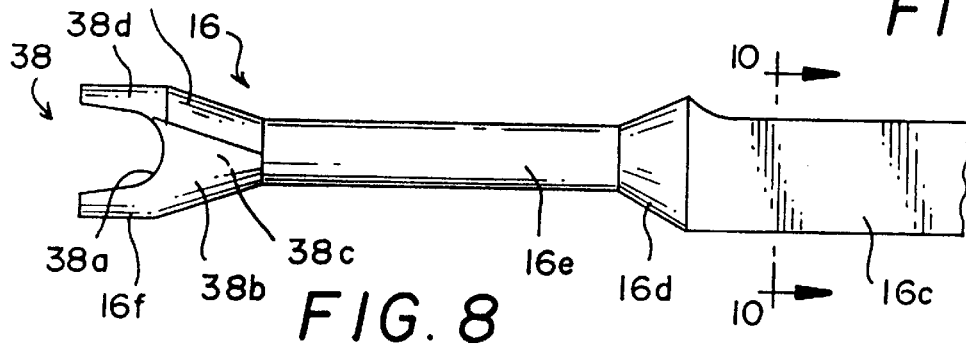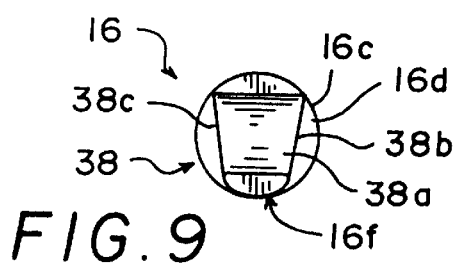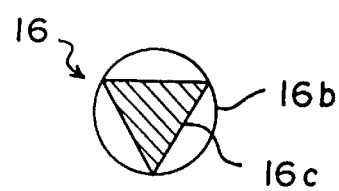

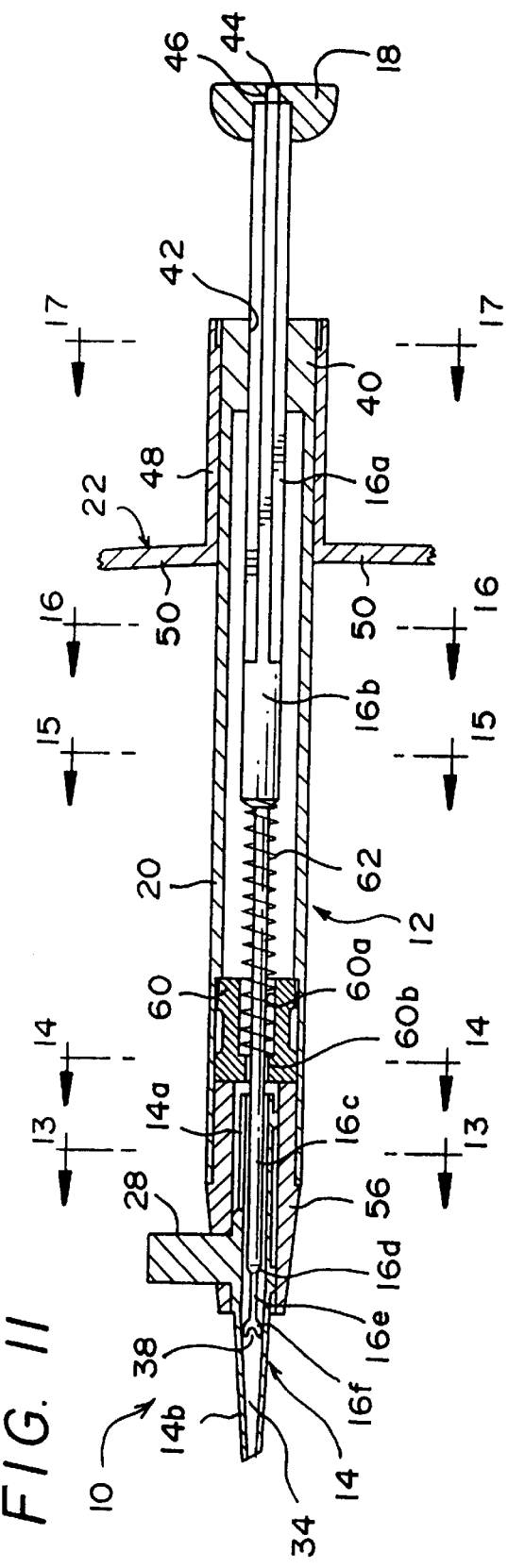

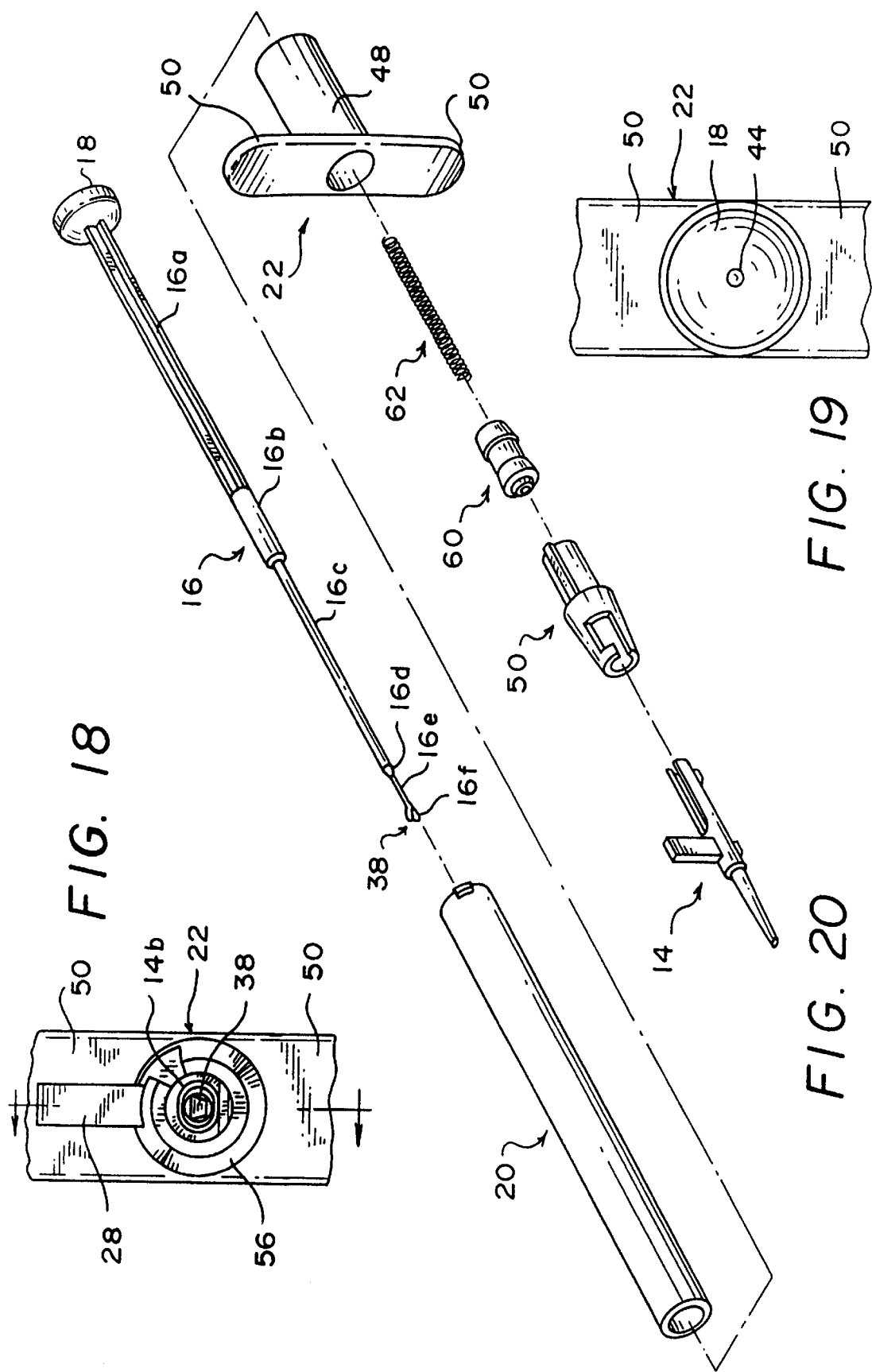

SPRING BIASED DEFORMABLE INTRAOCULAR INJECTING APPARATUS

RELATED APPLICATIONS

This application is a continuation of application Ser. No. 08/691,490, filed Aug. 2, 1996, now U.S. Pat. No. 5,860,984; and a Continuation-In-Part (CIP) of:

U.S. patent application entitled "Deformable Intraocular Lens Injecting Apparatus with Deformable Tip Plunger", Ser. No. 08/570,564, filed Dec. 11, 1995, now U.S. Pat. No. 5,772,666, and a CIP of U.S. Ser. No. 08/368,792, filed Jan. 4, 1995, pending; and a CIP of U.S. Ser. No. 08/196,855, filed Feb. 15, 1994, now U.S. Pat. No. 5,941,886, other Related applications are:

U.S. patent application entitled "Transverse Hinged Deformable Intraocular Lens Injecting Apparatus", Ser. No. 08/1547,908, filed Oct. 25, 1995; now U.S. Pat. No. 5,616,148;

U.S. patent application entitled "Transverse Hinged Deformable Intraocular Lens Injecting Apparatus, Ser. No. 08/547,295, filed Oct. 25, 1995; now U.S. Pat. No. 5,620,450;

U.S. patent application entitled "Deformable Intraocular Lens Injection System, and Method Thereof", Ser. No. 08/449,103, filed May 24, 1995; now abandoned;

U.S. patent application entitled "Deformable Intraocular Lens Injecting Device, Ser. No. 08/403,530, filed Mar. 14, 1995; now abandoned;

U.S. patent application entitled "Deformable Intraocular Lens Insertion System", Ser. No. 401,523, filed Mar. 10, 1995; now U.S. Pat. No. 5,807,400

U.S. patent application entitled "Disposable Intraocular Lens Insertion System, Ser. No. 08/345,360, filed Nov. 18, 1994; now abandoned;

U.S. patent application entitled "Intraocular Lens Insertion System", Ser. No. 08/240,520, filed Jul. 19, 1994; now abandoned;

U.S. patent application entitled "Deformable Intraocular Lens Insertion System", Ser. No. 08/221,013, filed Apr. 1, 1994, issued as U.S. Pat. No. 5,494,484;

U.S. patent application entitled "Method for the Surgical Implantation of a Deformable Intraocular Lens in the Eye", Ser. No. 08/220,999, filed Apr. 1, 1994, now abandoned;

U.S. patent application entitled "Deformable Intraocular Lens Cartridge", Ser. No. 08/197,604, filed Feb. 17, 1994, issued as U.S. Pat. 5,499,987;

U.S. patent application entitled "Methods of Implantation of a Deformable Intraocular Lens, Ser. No. 08/195,717, filed Feb. 14, 1994 now abandoned; and U.S. patent application entitled "Intraocular Lens Insertion System", Ser. No. 07/953,251, filed Sep. 30, 1992, now abandoned, all fully incorporated herein by reference.

FIELD OF INVENTION

The present invention is directed to lens injecting apparatus having a spring biased plunger used for the implantation of a deformable intraocular lens. The lens injecting apparatus according to the present invention can have a single component or multi-component design.

BACKGROUND OF THE INVENTION

STAAR Surgical Company of Monrovia, Calif. and STAAR Surgical A.G. of Switzerland have been developing and successfully placing into service intraocular lens injecting apparatus for many years. The use of these intraocular lens injecting apparatus have been widely accepted by Ophthalmic surgeons for implanting deformable type intraocular lenses. In particular, STAAR currently supplies a two (2) component lens injecting apparatus including a titanium or stainless steel lens injecting device and a plastic one-piece cartridge having a lens holding portion connected to a nozzle portion. This design has proved to be particularly successful.

SUMMARY OF THE INVENTION

A first object of the present invention is to provide a lens injecting apparatus with a spring biased plunger.

A second object of the present invention is to provide a one component deformable intraocular lens injecting apparatus with a spring biased plunger.

A third object of the present invention is to provide a multiple component deformable intraocular lens injecting apparatus with a spring biased plunger.

A fourth object of the present invention is to provide a lens injecting apparatus including a deformable intraocular lens injecting device with a spring biased plunger and a separate lens cartridge.

A fifth object of the present invention is to provide a deformable intraocular lens injecting apparatus with a spring biased plunger configured to provide biasing force against forward advance of the plunger.

A sixth object of the present invention is to provide a deformable intraocular lens injecting apparatus with a spring biased plunger configured to provide biasing force against forward advance of the plunger when the plunger is forcing and advancing the deformable intraocular lens through a delivery passageway of the lens injecting apparatus into the eye.

The present invention is directed to a deformable intraocular lens injecting apparatus with a spring biased plunger. A preferred embodiment of the lens injecting apparatus includes a spring biased plunger configured to exert a force on the plunger in an opposite rearward direction relative to the forward direction of advancing the plunger during use of the lens injecting apparatus.

The spring biased plunger of the preferred embodiment of the lens injecting apparatus can be configured to allow the plunger to automatically return to a full rearwardly extended position after a user has implanted the deformable intraocular lens into the eye. For example, in an embodiment configured so that the user's thumb exerts a forwardly directed force on the spring biased plunger, when the user decreases this force the plunger automatically begins to return to its full rearward position by the rearwardly directed force exerted on the plunger by the biasing spring.

The deformable intraocular lens injecting apparatus according to the present invention can be a single component design (i.e. one component when assembled requiring no disassembly for loading and injecting a deformable intraocular lens), or a multiple piece design having separate components for loading the deformable intraocular lens prior to assembly for then injecting the deformable intraocular lens (e.g. separate lens injecting device with lens cartridge receiver plus separate lens cartridge).

BRIEF DESCRIPTION OF THE DRAWINGS

FIG. 1 is a perspective view of a deformable intraocular lens injecting apparatus according to the present invention.

FIG. 2 is a blown-up perspective view of a forward end portion of the deformable intraocular lens shown in FIG. 1 with the lens cartridge removed and readied for insertion into the forward end of the lens injecting device.

FIG. 3 is a blown-up perspective view of a forward end portion of the deformable intraocular lens shown in FIG. 1.

FIG. 4 is a perspective view of a deformable intraocular lens cartridge according to the present invention for use with the deformable intraocular lens injecting device according to the present invention.

FIG. 5 is a front end view of the lens cartridge shown in FIG. 4.

FIG. 6 is a rear end view of the lens cartridge shown in FIG. 4.

FIG. 7 is a longitudinal cross-sectional view of the lens cartridge shown in FIG. 4.

FIG. 8 is a partial side elevational view of the plunger of the deformable intraocular lens injecting device according to the present invention showing the design of the plunger tip.

FIG. 9 is a front end view of the plunger tip shown in FIG. 8.

FIG. 10 is a cross-sectional view of the plunger, as indicated in FIG. 8.

FIG. 11 is a side longitudinal cross-sectional view of the lens injecting apparatus shown in FIG. 1 with the plunger fully extended during non-use.

FIG. 12 is a side longitudinal cross-sectional view of the lens injecting apparatus shown in FIG. 2 with the plunger fully advanced during use.

FIG. 18 is a front end elevational view of the lens injecting apparatus shown in FIG. 1.

FIG. 19 is a rear end elevational view of the lens injecting apparatus shown in FIG. 1.

FIG. 20 is a broken away perspective view of the lens injecting apparatus shown in FIGS. 1 to 19 disassembled.

DETAILED DESCRIPTION OF PREFERRED EMBODIMENTS

Figure 15:
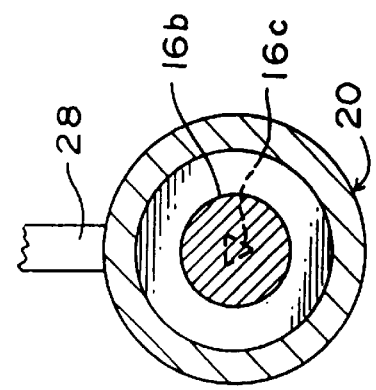
FIG. 15 is a transverse cross-sectional view through the lens injecting apparatus as indicated in FIG. 11.
Figure 14:
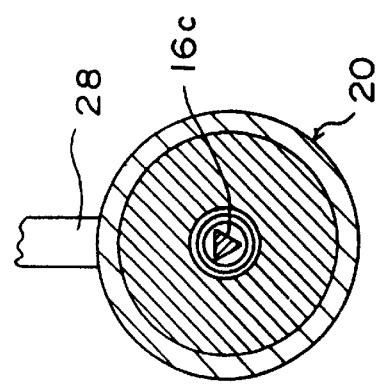
FIG. 14 is a transverse cross-sectional view through the lens injecting apparatus as indicated in FIG. 11.
Figure 13:
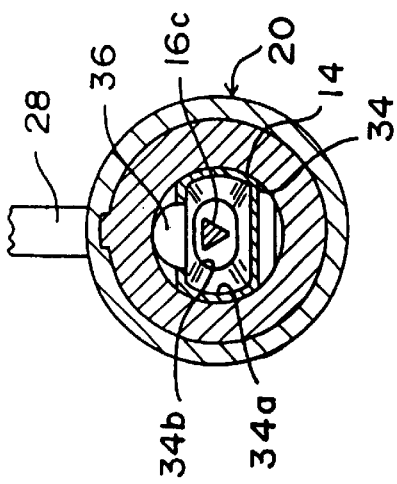
FIG. 13 is a transverse cross-sectional view through the lens injecting apparatus as indicated in FIG. 11.

A preferred deformable intraocular lens injecting apparatus 10 according to the present invention is shown in FIGS. 1 to 3.

The lens injecting apparatus 10 is a two (2) component design including 1) a separate lens injecting device 12; and 2) a separate lens cartridge 14, which separate components can be assembled together after loading a deformable intraocular lens into the lens cartridge 14 to define the assembled lens injecting apparatus readied for the implantation operation. The parts of the lens injecting apparatus are preferably made of autoclavable plastic (e.g. polysulfone, nylon), however, some or all parts can be made of metal (e.g. titanium, stainless steel). In a most preferred embodiment, the parts are all plastic except for a coiled metal spring for biasing the plunger.

The lens injecting device 12 includes a spring-biased plunger 16 having a thumb grip 18 slidably disposed within a tubular body 20. The tubular body 20 is defined by a cylindrical body portion 20a and a cone-shaped body portion 22. In the embodiment shown, the cylindrical body portion 20a and cone-shaped body portion 22 are separate components assembled together. However, the tubular body 20 can be made as a one-piece integral unit.

The lens injecting device 12 further includes a finger grip 22 connected to or extending from the tubular body 20. In the embodiment shown, the finger grip 22 is a separate component assembled to the tubular body 20. However, the finger grip 22 can be an integral portion of the tubular body in an alternative embodiment.

The cone-shaped body portion 20b of the tubular body 20 is provided with a lens cartridge receiver 24. The lens cartridge receiver 24 is defined by an opening 24a in a forward end of the cone-shaped body portion 20b leading into a cylindrical-shaped passageway 24b extending through the cone-shaped body portion 20b. The cone-shaped body portion 20b is also provided with a slot 26 defined by a longitudinal slot portion 26a extending into a transverse slot portion 26b.

The lens cartridge 14 is defined by a lens holding portion 14a and a nozzle portion 14b. In the embodiment shown, the lens holding portion 14a and the nozzle portion 14b are a one-piece integral part made for example by plastic injection molding. However, the lens holding portion 14a and the nozzle portion 14b can be made as separate components and then assembled together. Further, the lens cartridge 14 is provided with an extension 28 and a nozzle tip 30. In the embodiment shown, the extension 28 is molded as an integral portion of the one-piece integral lens cartridge 14. However, the extension can be made as a separate part and then assembled to a remaining portion of the lens cartridge. In addition, the nozzle tip 30 can be provided with a beveled edge 32, or alteratively, with a transverse oriented edge, slot(s) and/or zones to allow expansion, and other tip modifications as desired.

The lens cartridge 14 interconnects into the lens cartridge receiver 24 of the lens injecting device by means of a "bayonet" type connection. Specifically, to interconnect the lens cartridge 14 and lens injecting device 12, the back end of the lens cartridge 14 is fitted into the forward end of the lens cartridge receiver 24 and then lens cartridge 14 is moved rearwardly so that the extension 28 is moved into the longitudinal slot portion 26a. The lens cartridge 14 is then twisted relative to the lens injecting device 12 so that the extension 28 is moved into the transverse slot portion 26b securely locking the lens cartridge inside the lens injecting device 12, as shown in FIG. 2.

The detailed construction of a preferred lens cartridge 14 according to the present invention is shown in FIGS. 4 to 7. The lens cartridge 14 shown is a "hingeless" type design, however, a "hinged" type lens cartridge can be utilized. Further, the lens cartridge 14 is a one-piece integral design made, for example, by plastic injection molding.

The lens cartridge 14 is provided with a lens delivery passageway 34 extending therethrough, as shown in FIG. 7.

Specifically, the lens delivery passageway 34 includes a passageway portion 34a extending through lens holding portion 14a and a passageway portion 34b extending through lens holding portion 14b. The lens delivery passageway 34 tapers inwardly in a forward direction of implantation of the deformable intraocular lens. Further, the lens delivery passageway 34 is defined by an oval transverse cross-sectional shape along its length, as shown in FIG. 6.

The configuration of the lens delivery passageway 14 is particularly important for the function of compressing, folding or otherwise decreasing the cross-sectional size of the deformable intraocular lens as it is force through the lens delivery passageway 34 by the plunger 16. The inwardly tapering configuration of the lens delivery passageway 14 further compresses or folds the deformable intraocular lens as it is advanced through the lens delivery passageway 14. The lens delivery passageway can also be contoured to further compress or fold the deformable intraocular lens. For example, the lens delivery passageway can be provided with at least one groove to further effected folding of a portion of the deformable intraocular lens, in particular by gripping an edge of the edge and forcing the edge inwardly as the deformable intraocular lens is advanced through the lens delivery passageway.

The lens holding portion 14a of the lens cartridge 14 is provided with an upper slot 36, as shown in FIGS. 4 and 6. The slot 36 facilitates the loading of the deformable intraocular lens into the lens cartridge 14, specifically into the lens delivery passageway 34. For example, the deformable intraocular lens can be positioned above the upper slot 36 resting on the edges 36a of the slot 36, and then the center of the deformable intraocular lens can be forced downwardly (e.g. with closed tips of forceps) to load the deformable intraocular lens into the lens delivery passageway 34. Alternatively, the deformable intraocular lens can be initially folded with a pair of lens folding forceps, and then loaded through the open end 34c (See FIG. 7) of the lens holding portion 14a of the lens cartridge 14. In this lens loading procedure, the tips of the forceps are moved into the lens delivery passageway portion 34a with the slot 36 accommodating the closed forceps so that the deformable intraocular lens is advanced and loaded into a forward portion of the lens portion 34a (i.e. to position ahead of slot 36 where the wall of the lens delivery passageway portion 34a is closed).

A detailed construction of the plunger 16 is shown in FIGS. 8 to 12. The plunger 16 shown has a one-piece integral design, however, the plunger 16 can be made of separate parts assembled together.

The plunger 16 includes a first main plunger portion 16a, second main plunger portion 16b, a first extension plunger portion 16c, a transition plunger portion 16d, a second extension plunger portion 16e, and a plunger tip portion 16f (See FIG. 11). The plunger 16 is slidably supported inside the tubular body 20 of the lens injecting device 12. Specifically, the tubular body 20 includes a sleeve portion 40 (FIG. 11) located at the rear end thereof for slidably supporting the plunger 16. The sleeve portion 40 is an integral portion of the tubular body made, for example, by plastic injection molding. However, the sleeve portion 40 can be made as a separate part assembled to the tubular body 20.

Figure 16:
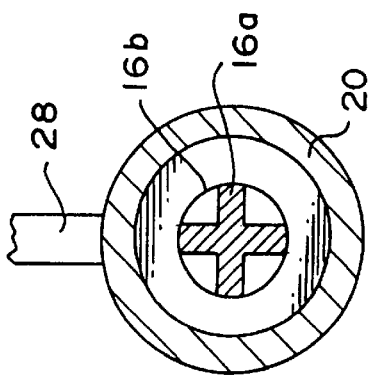
FIG. 16 is a transverse cross-sectional view through the lens injecting apparatus as indicated in FIG. 11.

The outer dimensions of the first main plunger portion 16a are just slightly less than the inner dimensions of a passageway 42 extending through the sleeve portion 40 of the tubular body 20 to slidably support the plunger 16. Further, the transverse cross-sectional shape of the first main plunger portion 16a and the passageway 42 are shaped to act as a keyway to prevent relative rotation of the plunger inside the tubular body 20 for maintaining a fixed orientation of the plunger tip portion 16f relative to the lens delivery passageway 34 through the lens cartridge 14. For example, the transverse cross-sectional shape of the first main plunger portion 16a and the passageway 42 are cross-shaped as shown in FIG. 16 and dimensioned so that the first main plunger portion 16a nests within the passageway 42 to allow sliding therebetween. However, other suitable keyway shapes and configurations can be substituted for the cross-shaped configuration shown.

The second main plunger portion 16b has a circular transverse cross-sectional shape (FIGS. 15 and 16), the first extension plunger portion 16c has a triangular transverse cross-sectional shape (FIGS. 10, 13, 14 and 15), the transition plunger portion 16d is conical-shaped, and the second extension plunger portion 16e has a circular transverse cross-sectional shape (FIG. 20). However, the transverse cross-sectional shapes of these plunger portions can be modified or changed depending on a particular plunger design.

The second extension plunger portion 16e has an outer transverse cross-sectional size smaller relative to the first extension plunger portion 16c and the plunger tip portion 16f so that when the plunger tip portion 16e and the second extension plunger portion 16e are positioned inside the lens delivery passageway 34 of the lens cartridge 14, there exists an annular space between the outer surface of the second extension plunger 16e and the inner surface of the lens delivery passageway 34 to accommodate the trailing haptic of the loaded deformable intraocular lens.

The plunger tip portion 16f is defined by a faceted tip 38 including a concave surface facet 38a, a left side inclined surface facet 38b, a right side inclined surface facet 38c, a cylindrical surface facet 38d, and a conical surface facet 38e. The concave surface facet 38a is configured to grip a trailing edge of the deformable intraocular lens, and the inclined surface facets 38b and 38c are configured to manipulate the deformable intraocular lens once inside the eye.

The rear end of the plunger 16 is provided with an extension 44 configured to snap fit together with the thumb grip 18. Specifically, the thumb grip 18 is provided with a through hole 46 for receiving the extension 44. The through hole 46 and the extension 44 are configured (e.g. provided with interlocking tabs or edges or interference fit) so that the plunger 16 can be assembled by simply pressing the extension 44 into the through hole 46.

The detailed construction of the lens injecting apparatus 10, in particular the lens injecting device 12, is shown in FIGS. 11 to 20.

Figure 17:
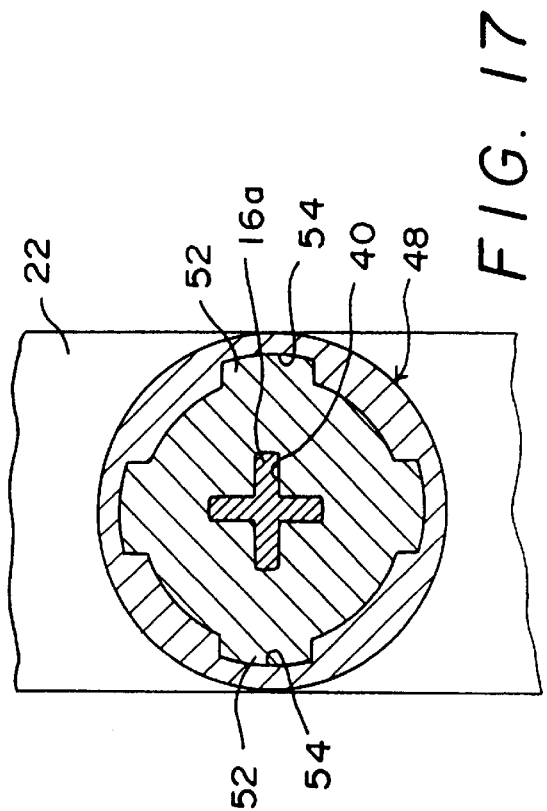
FIG. 17 is a transverse cross-sectional view through the lens injecting apparatus as indicated in FIG. 11.

The rear end of the lens injecting device 12 is fitted with the finger grip 22 (FIG. 11). The finger grip 22 includes an outer sleeve 48 provided with a pair of gripping ears 50 for cooperating with the fore finger and middle finger of a user. The outer surface of the rear end of the tubular body 20 of the lens injecting device 12 is splined to the outer sleeve 48, as shown in FIG. 17. Specifically, the outer surface is provided with a pair of opposed protrusions 52, 52 interlocking with a pair of opposed grooves 54 provided in the inner surface of the outer sleeve 48 of the finger grip 22. The finger grip 22 can be press fit, adhered, weld or otherwise suitably mechanically connected in the assembled lens injecting device 12.

The front end of the lens injecting device 12 is provided with a cone-shaped plug 56 having an inner sleeve portion 58 fitting inside and connecting with the front end of the tubular body 20 (FIG. 11). The sleeve portion 58 can be press fit (interference fit), snap fit, adhered, weld or otherwise mechanically connected to the tubular body 20. The cone-shaped plug 56 is provided with a passageway 24a (FIG. 3) defining the lens cartridge receiver 24.

A sleeve 60 shown as being made of metal is disposed within the front end of the tubular body 20 (FIG. 11) and located adjacent to the cone-shaped plug 56. Alternatively, the sleeve 60 can be made of plastic. The sleeve 60 is mechanically connected (i.e. anchored) inside the tubular body 20 to prevent any relative sliding movement, since the sleeve 60 functions as one stop for the spring. The sleeve 60 is provided with a larger diameter passageway portion 60a for accommodating a forward end of the spring 62 and a smaller diameter passageway 60b for slidably supporting the first extension plunger portion 16c of the plunger 16. The larger diameter passageway portion 60a and the spring 62 can be sized so that the front end of the spring is interference fit and anchored to the sleeve 60.

The transition between the second main plunger portion 16b and the first extension plunger portion 16c defines another stop for the spring 62. The spring 62 is shown located between the stops at opposite end of the spring 62 (FIG. 11). The length of the spring 62 or the configuration of the stops can be selected so that the plunger 16 is moved a predetermined initial distance prior to spring engagement, or already engage without any movement of the plunger 16 a predetermined initial distance. However, it is particularly preferred that the configuration is selected and designed so that the spring 62 is already engaged to some extent before the plunger tip portion 16f makes contact with the loaded deformable intraocular lens. This arrangement provide a certain feel and control over the advancement of the plunger 16 by the user facilitating use thereof. Further, the spring arrangement is preferably designed to substantially fully retract the plunger 16 to its starting position after the user lets up or fully releases the thumb grip 18.

The spring 62 is shown as a coiled spring, preferably made of metal. Importantly, the spring 62 can be replace with other spring systems and arrangements. For example, a section of resilient plastic tubing can be substituted for the spring 62. Further, a metal or elastic cantilever spring can be utilized, or combination of the same or various types of conventional and custom designed springs.

FIG. 20 shows the separate components or parts of the lens injecting apparatus 10. These components are assembled together to form the two (2) component design including the lens injection device 12 and lens cartridge 14.

Figure 21:
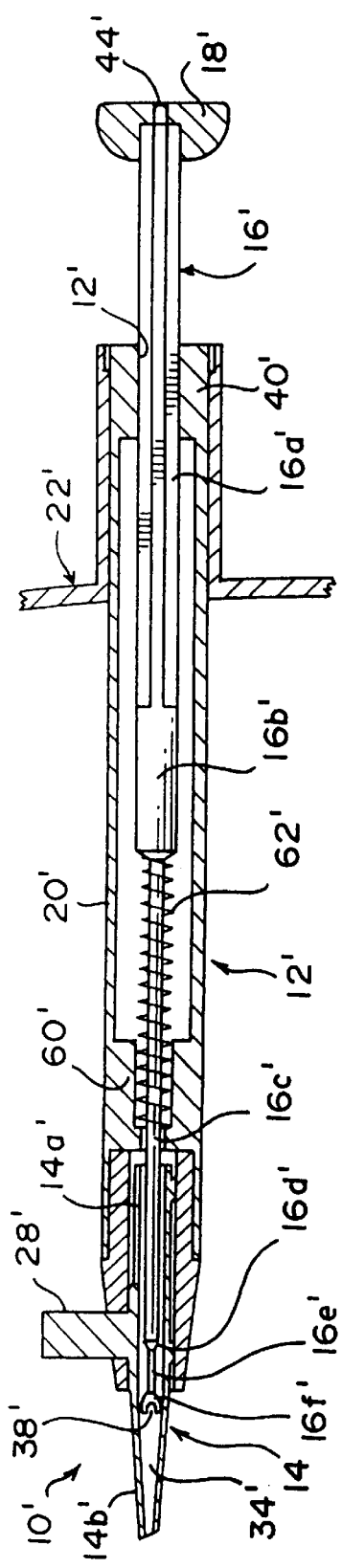
FIG. 21 is a longitudinal cross-sectional view of another embodiment of the lens injecting apparatus according to the present invention having a tubular body with an integral sleeve portion functioning as a stop for the spring.

Another embodiment of the lens injecting apparatus 10' is shown in FIG. 21. In this embodiment, the sleeve 60' is formed as an integral portion of the tubular body 20. For example, the tubular body 20 is injection molded of polysulfone with the integral sleeve 60".

Figure 22:
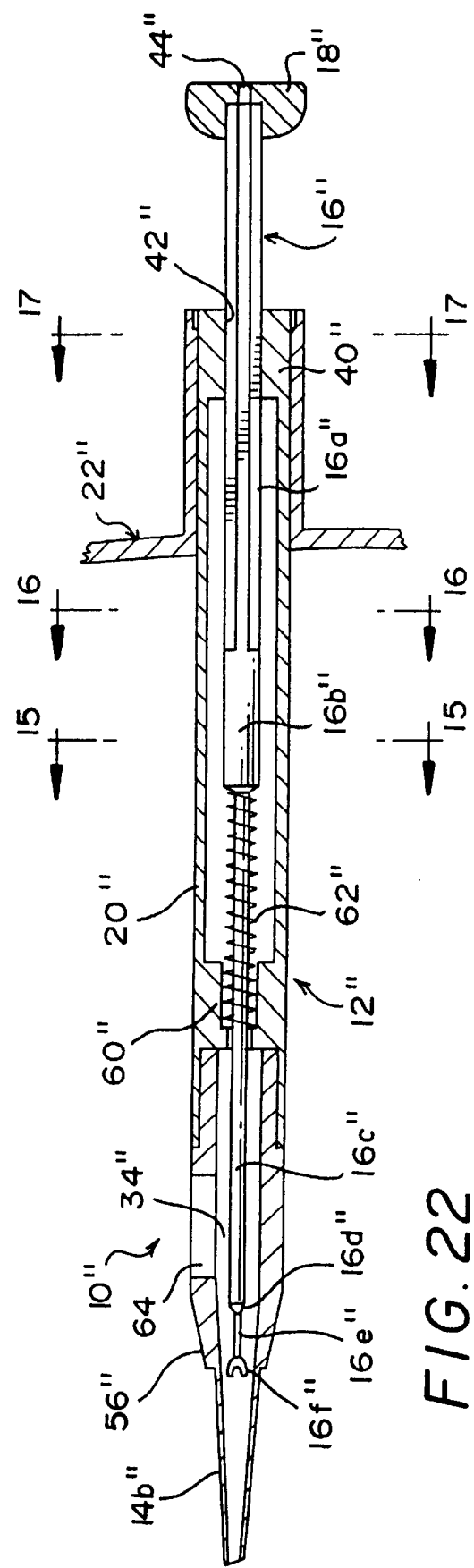
FIG. 22 is a longitudinal cross-sectional view of a further embodiment of the lens injecting apparatus according to the present invention having a one (1) component design after assembly.

A further embodiment of the lens injecting apparatus 10" is shown in FIG. 22. This is a one (1) component design doing away with a separate lens cartridge. The cone-shaped nozzle portion 56" and the nozzle portion 14b" are molded as a one-piece integral part, and provided with an open lens receiver 64 to allow the deformable intraocular lens to be directly loaded into the lens delivery passageway 34", for example with a forceps (not shown). The lens receiver 64 can be provided with a slot 66 to allow the forceps to be moved forward inside the lens receiver while gripping the deformable intraocular lens to load the lens forward in or partially into the nozzle portion 14b".

We claim:

1. A deformable intraocular lens injecting apparatus for inserting a deformable intraocular lens through a small incision into an eye, said apparatus comprising:
    a lens injecting device including a lens delivery passageway for accomodating the deformable intraocular lens, said lens injecting device including a lens cartridge receiver;
    a sleeve portion disposed within said lens injecting device;
    a plunger slidably disposed within said sleeve portion;
    a spring connected between said sleeve portion of said lens injecting device and said plunger for biasing said plunger rearwardly when being advanced forward by a user;
    a lens cartridge removably disposed within said lens cartridge receiver of said lens injecting device;
    wherein said lens injecting apparatus includes including a locking arrangement between said lens cartridge and said lens injecting device; and
    wherein said locking arrangement is defined by providing said lens cartridge with an extension which cooperates with a L-shaped slot provided in the lens cartridge receiver of said lens injecting device.

2. An apparatus according to claim 1, wherein said spring is mounted on said plunger.

3. An apparatus according to claim 2, wherein said spring is a coiled spring mounted on a portion of said plunger.

4. An apparatus according to claim 3, wherein said spring is located inside said lens injecting device.

5. An apparatus according to claim 4, wherein said spring is positioned between a stop on said plunger and a stop inside said lens injecting device.

6. An apparatus according to claim 5, wherein said stop on said plunger is defined by a transition between a portion of said plunger having a smaller transverse cross-sectional size and a portion of said plunger having a larger transverse cross-sectional size.

7. An apparatus according to claim 6, wherein said spring functions during a portion of said stroke of said plunger when a tip of said plunger is forcing the deformable intraocular lens through the lens delivery passageway through the lens injecting apparatus.

8. An apparatus according to claim 5, wherein said stop inside said housing is defined by a sleeve portion slidably accommodating a portion of said plunger.

9. An apparatus according to claim 1, wherein said spring functions during at least a portion of a stroke of said plunger.

10. An apparatus according to claim 1, wherein said plunger has a tip including an end face provided with a transverse slot for gripping an edge of the deformable intraocular lens.

11. An apparatus according to claim 1, wherein said lens cartridge includes a lens holding portion connected to a nozzle portion.

12. An apparatus according to claim 1, wherein said sleeve portion is a separate component assembled inside said lens injecting device.

13. An apparatus according to claim 1, wherein said sleeve portion and said lens injecting device are a one-piece integral arrangement.

14. An apparatus according to claim 13, wherein said lens injecting device and said sleeve portion are a plastic injection molded component.

15. An apparatus according to claim 1, wherein said lens cartridge comprises a lens holding portion connected to a nozzle portion.

16. A deformable intraocular lens injecting apparatus for inserting a deformable intraocular lens through a small incision into an eye, said apparatus comprising:

- a lens injecting device including a lens delivery passageway for accommodating the deformable intraocular lens, said lens injecting device including a lens cartridge receiver;
- a sleeve portion disposed within said lens injecting device;
- a plunger slidably disposed within said sleeve portion;
- a spring connected between said sleeve portion of said lens injecting device and said plunger for biasing said plunger rearwardly when being advanced forward by a user;
- a lens cartridge removably disposed within said lens cartridge receiver of said lens injecting device;
- wherein said lens injecting device comprises a body portion having said lens cartridge receiver, said lens cartridge defining said lens delivery passageway;
- wherein said lens cartridge comprises a lens holding portion connected to a nozzle portion; and
- wherein said lens injecting apparatus includes a bayonet-type locking arrangement between said lens cartridge and said body portion.

17. An apparatus according to claim 16, wherein said bayonet-type locking arrangement includes an extension on said lens cartridge cooperating with an L-shape slot provided in said lens cartridge receiver of said lens injecting device.

* * * * *